United States Patent [19]

Taliaferro

[11] Patent Number: 4,866,383
[45] Date of Patent: Sep. 12, 1989

[54] METHOD AND APPARATUS HAVING LOAD CELL RESPONSIVE TO MOVEMENT OF A MAGNETIC FIELD GENERATOR FOR DIFFERENTIATING BETWEEN MATERIALS

[76] Inventor: Sam W. Taliaferro, 0361 County Rd. 400, Breckenridge, Colo. 80424

[21] Appl. No.: 177,356

[22] Filed: Apr. 1, 1988

[51] Int. Cl.⁴ .................. G01N 27/72; G01R 33/00; G01B 7/16
[52] U.S. Cl. .................. 324/228; 73/763; 324/207; 324/226; 324/235; 361/180
[58] Field of Search ............ 324/207, 208, 226, 228, 324/235, 239–243; 361/180; 73/760, 763, 774, 775, 779

[56] References Cited

U.S. PATENT DOCUMENTS

| | | | |
|---|---|---|---|
| 3,002,149 | 9/1961 | Christian | 324/228 |
| 3,065,412 | 11/1962 | Rosenthal | 324/239 |
| 4,232,265 | 11/1980 | Smirnov | 324/244 |
| 4,310,797 | 1/1982 | Butler | 304/228 |
| 4,314,202 | 2/1982 | Okubo | 324/228 X |
| 4,409,548 | 10/1983 | Focht | 324/208 X |
| 4,517,514 | 5/1985 | Howell | 324/228 X |
| 4,677,378 | 6/1987 | Tokura et al. | 324/208 |
| 4,684,888 | 8/1987 | Tabak | 324/225 X |
| 4,758,788 | 7/1988 | Weiss et al. | 324/243 |

Primary Examiner—Gerard R. Strecker
Attorney, Agent, or Firm—Sheridan, Ross & McIntosh

[57] ABSTRACT

The invention relates to an apparatus consisting of a device for generating a magnetic field mounted for movement relative to a product sitting in or moving through its field which is suspected of carrying at least one metal component which will cause the generator to move either toward or away therefrom because of either the attractive or repulsive forces, or both, caused by the presence of this metal or these metals. A load-responsive element in the form of a load cell is connected to the field generator so as to sense its movememnt if any and output a signal evidencing such movement. A detector is connected to receive the output signal from the load cell and use this information to initiate an appropriate response to the presence of the metal or metals causing the displacement of the generator. The invention also encompasses the method for detecting the presence of one or more metals, both ferrous and conductive, which will either attract or repel a generator of a magnetic field when within its field or moving through it. The resulting movement, if any, is detected by a load cell and used as an indication of the presence or absence of the metals causing displacement of the generator.

22 Claims, 4 Drawing Sheets

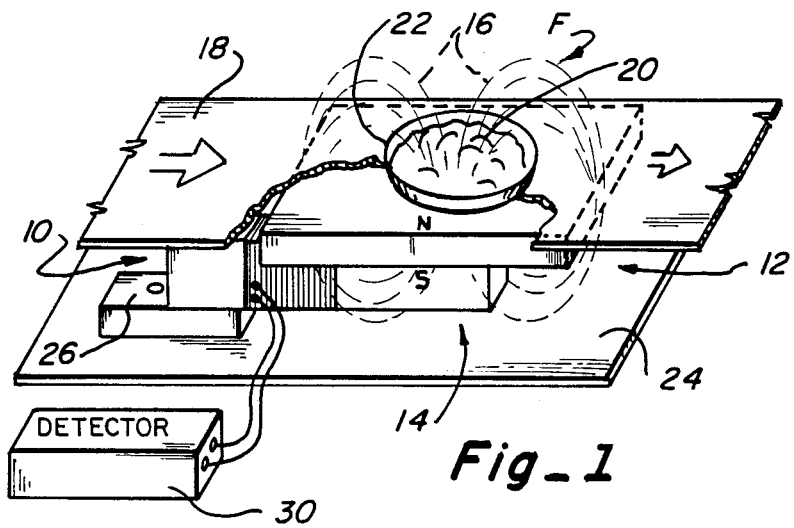
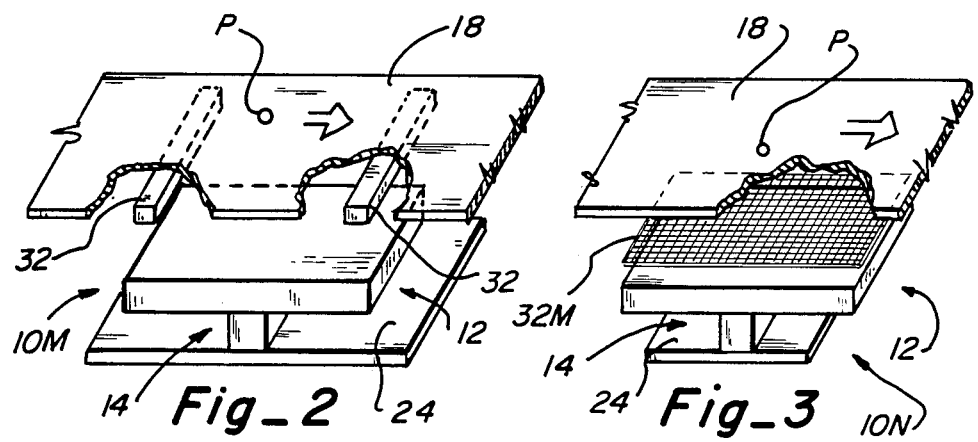
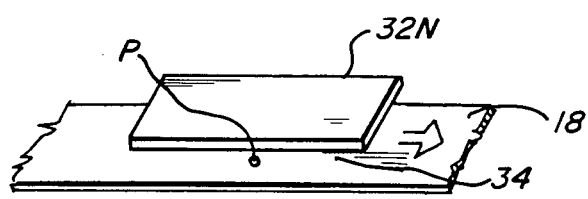
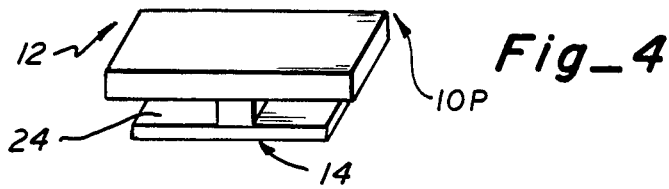

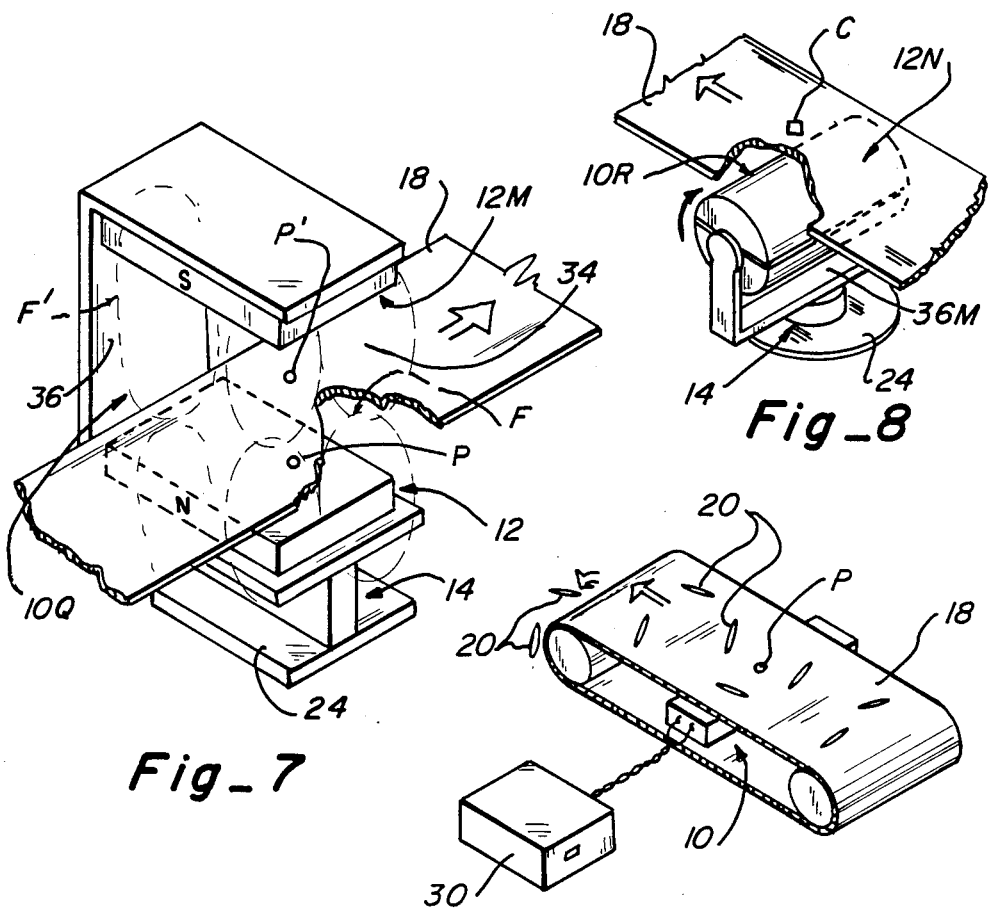

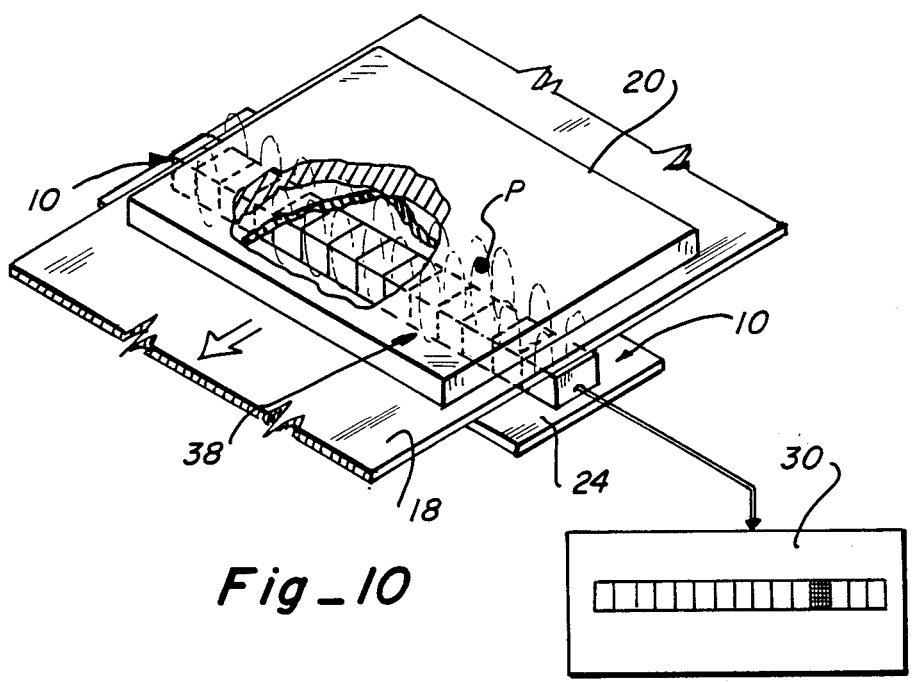
Fig_10
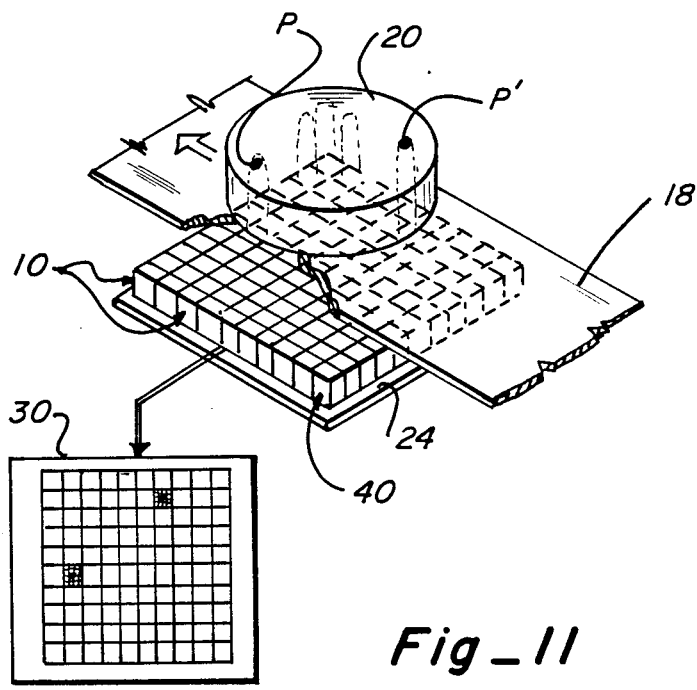
Fig_11

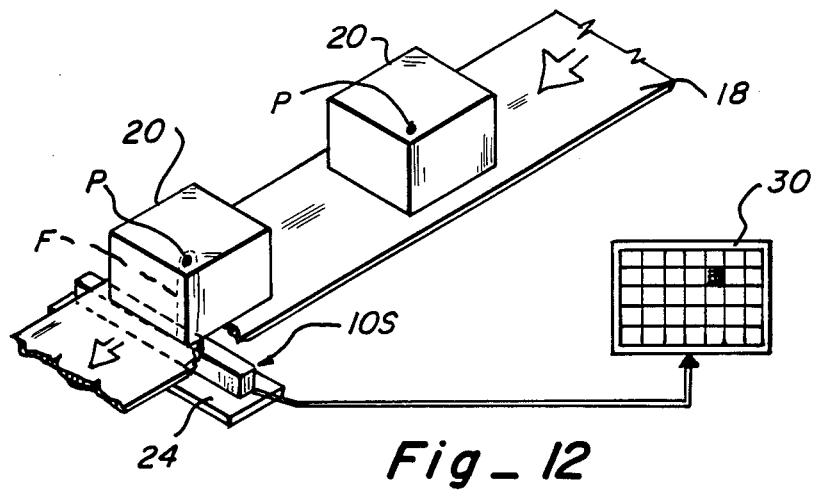
Fig_12
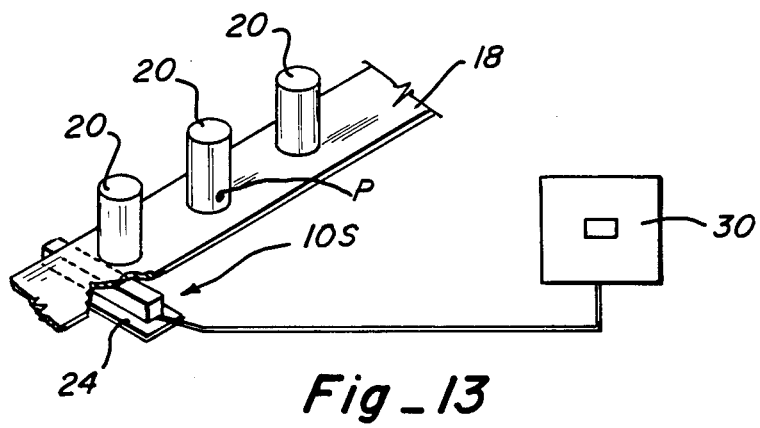
Fig_13
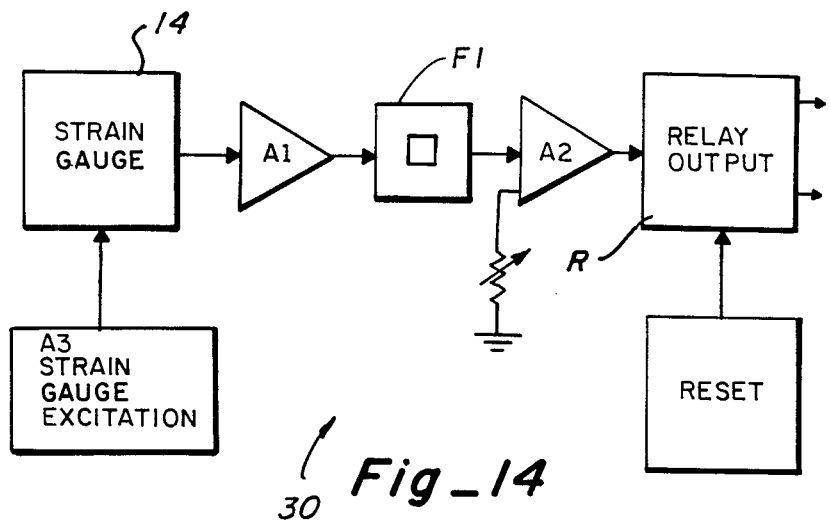
Fig_14

METHOD AND APPARATUS HAVING LOAD CELL RESPONSIVE TO MOVEMENT OF A MAGNETIC FIELD GENERATOR FOR DIFFERENTIATING BETWEEN MATERIALS

BACKGROUND OF THE INVENTION

Many applications exist today in which a need arises for detecting the presence of both ferrous and non-ferrous metal objects in non-metallic materials like, for example, food products, cereal grains, forest by-products used in the manufacture of building materials, chemicals and even finished goods. Generally speaking, these applications all involve the detection of unwanted contaminants which, if left undetected, could give rise to lawsuits or, perhaps, significant damage to delicate machinery downstream of the metal detection apparatus.

Other situations exist where the ferrous metal or stainless steel object is not a contaminant at all, but rather, a necessary part of an assembly. It becomes important to know, therefore, that the part is there and that it is in the right location, or both. An example might be a plastic or non-ferrous metal part assembled automatically containing a critical ferrous metal spring that may even be hidden from view and, therefore, impossible to locate visually.

Fortunately, metal detection systems already exists which are reasonably effective in recognizing, and oftentimes even removing, metal contaminants contained within non-metallic materials regardless of whether the contaminant is a ferrous or a non-ferrous metal. Such systems frequently include a transmitter coil and a pair of receiver coils placed in close proximity to the latter. The transmitter coil puts out a high frequency signal which is altered sufficiently in the presence of a metal object moving relative thereto, regardless of whether it is of a ferrous or a non-ferrous material, such that the resultant change it undergoes can be picked up by the receiver coils which then initiate some remedial action.

The problem with detectors of this type is that no metal object can be located within approximately a yard of the detection coils without it being subject to false signals indicating the presence of the metal being detected. This means, of course, that the system is incapable of finding a metal object in, for example, a food product packaged in an aluminum container passing through the aperture. As a matter of fact, these systems cannot be used with metal chutes or ducts, most especially those in which the metal carrier is interposed between the detection apparatus and the product being tested.

In my copending application Ser. No. 177,358, filed April, 1988 . I disclose a system for detecting the presence of ferrous metal contaminants in non-metallic materials being moved on or in magnetically transparent, but stationary, metal carriers; however, even this system, unique as it is, is ill-suited for use in the detection of ferrous metal and/or stainless steel ones contained within a non-ferrous metal object of some description like an aluminum pan or a metal object cast or otherwise made from a magnetically-transparent metal. An even greater problem exists in differentiating between like metals in a product, i.e. a ferrous metal part present in a ferrous metal assembly.

Accordingly, an urgent need exists for a metal detection system which can, in fact, reliably discriminate between ferrous and non-ferrous metals; like metals in the same product, either ferrous or non-ferrous; or even the position of a metal part or object within an assembly made of a dissimilar material, metal or otherwise.

1. Field of the Invention

The present invention relates, therefore, to a novel method and apparatus for discriminating between the same or different metals in the same product. The invention is also capable of detecting the amount or location or both of a one metal with respect to another which differs therefrom in its magnetic properties.

2. Description of the Related Art

The closest and most pertinent prior art known to applicant is that mentioned above which comprises a transmitting coil operative to generate a field in the area through which the product being tested must pass and a pair of detector coils which are responsive to any disturbance in this field due to the presence of metal objects and operative to set off an alarm or initiate some other corrective action. Insofar as applicant is aware, no system yet exists which is capable of differentiating between like or unlike metal materials in the way his does nor is any prior art magnetic system known to him which is capable of telling whether a given metal, be it magnetic or otherwise, is present in the proper proportions. There are, of course, systems which weigh an object, X-ray it, test the shape thereof or otherwise analyze one or more of its properties, dimensions or other of its parameters in order to ascertain whether or not it meets specifications; however, none of these prior art systems, at least insofar as applicant is aware, involves as his does using the deflection taking place in a generator of a magnetic field mounted atop a load cell as a reliable and accurate indication of some anomaly in the product being tested. The detection of conductive metals requires that they move relative to the magnetic field; whereas, those which are used in the detection of ferrous materials are effective regardless of whether the object being tested is moving or standing still.

Applicant is also aware of certain U.S. patents which employ generators of magnetic or electromagnetic fields which generate an output signal in response to the presence or movement of an outside instrumentality. The Okubo U.S. Pat. No. 4,314,202 senses the flexural vibration of a structural member located within the field while the Junker et al U.S. Pat. No. 4,528,856 generates a signal measuring the stress in a magnetic workpiece. Neither of these systems has as their objective that of metal detection nor would they function on such an application without complete redesign. U.S. Pat. No. 4,310,797 is somewhat more pertinent in that it relates to a so-called "stud finder" which employs a permanent magnet responsive to the presence of a ferrous metal object to close a switch and turn on a light. While the magnet does move in the presence of a ferrous metal part, no load-responsive element is a part of the combination. Finally, the Smirnov U.S. Pat. No. 4,232,265 is the most pertinent in that it employs two ferromagnetic plates, one fixed and the other movable with the movable one being mounted upon a strain gauge. The intensity of the interfering fields is quantified by the output signal keyed to the movement of the strain gauge. Here again, the application for which the system is designed is one of measuring the intensity between two interacting magnetic fields in a bench-type fixed system, not an industrial environment where the products are oftentimes moving, are rarely if ever ferromagnetic and may not even include a ferrous metal although capable of sensing the presence of a conductive one.

SUMMARY OF THE INVENTION

Applicant has discovered that, quite unexpectedly, the foregoing and other problems associated with the need to discriminate between two or more metals of different types in the same product, or even different amounts of the same metal, irrespective of whether the metals are magnetic or non-magnetic, can be accomplished by the simple, yet unobvious, expedient of mounting a field generator atop a load-sensitive transducer or so-called "load cell" and detecting the movement of the generator in response to the presence of a metal object within its force field. By simply setting the system to ignore loads of a given magnitude, the system becomes capable of detecting the presence of metal objects, be they magnetic or otherwise, which upset this predetermined relationship either by drawing the field generator closer to the object being tested or pushing it away. By providing an array of independent field generator/load cell subassemblies, the location of metal objects within a product can be determined along with other useful information such as, for example, whether or not the product is properly oriented relative to some reference or, perhaps, whether some metallic part is missing altogether. As far as discriminating between metals of like or different magnetic properties, probably one of the most utilitarian applications is that of detecting metal contaminants in food products packaged in aluminum trays. While it is, obviously, easier to detect a ferrous metal contaminant in such an environment since its magnetic properties are so different from that of aluminum which is essentially magnetically transparent; nevertheless, it is possible to even detect another aluminum contaminant since, when it moves, it will cause an eddy current to be introduced into the field of the permanent magnet that adds to that of the tray, the latter presumably being below the background threshold at which the system will trigger by itself.

Accordingly, it is the principal object of the present invention to provide a novel and improved method and apparatus for discriminating between metals having different magnetic properties as well as to differentiate between discrete portions of those having the same magnetic properties.

A second objective of the invention it to provide a method and apparatus of the class described which can be used to detect anomalies in both metal and non-metallic products that are missing one or more parts or are otherwise defective.

An additional object of the invention herein disclosed and claimed is that of providing a magnetically-sensitive system responsive under certain circumstances to the presence of a metal, both ferrous and otherwise, that is capable of even quantitative determinations.

Another objective is to provide a metal detection sensor subassembly which when used in a spatially-dispersed array, can provide positional information concerning the location of a metal element or component or contaminant.

Still another object is that of providing information concerning the relative proportions of two different metals, one magnetic and the other non-magnetic, contained within the same sample.

Additional objects are to provide an apparatus for detecting metal anomalies which is simple, easy to use, reliable, versatile, compact, sensitive and is relatively inexpensive as well as being one which requires no special skills or training to learn to operate.

Other objects will be in part apparent and in part pointed out specifically hereinafter in connection with the description of the drawings which follows.

FIG. 1 is a perspective view showing the field generator/load cell sensor positioned beneath a magnetically-transparent support carrying the product being tested;

FIG. 2 is a schematic view showing a first modification of the sensor subassembly wherein some ferrous metal bars are used to lighten the load on the load cell and thus permit the use of a smaller and, therefore, more sensitive cell;

FIG. 3 is a schematic view showing a second modification of the sensor subassembly employing a ferrous metal screen to reduce the load on the load cell;

FIG. 4 is a schematic view showing a third modification of the sensor subassembly wherein a fixed ferrous metal plate is spaced above the assembly and used in combination therewith to not only lighten the load on the load cell but, in addition, to concentrate the field in the detection area;

FIG. 5 is a diagram showing the shape of the field generated by the sensor subassemblies of FIGS. 1, 2 and 3;

FIG. 6 is a diagram showing the shape of the field concentrated in the detection area by the addition of the fixed plate in the assembly of FIG. 4;

FIG. 7 is a schematic view showing a still further modified sensor subassembly wherein the scanning area is substantially increased;

FIG. 8 is a schematic view showing yet another modification of the sensor subassembly which is specifically designed to increase the effect of the eddy currents generated by small non-ferrous conductive parts as they move through the field;

FIG. 9 is a schematic view showing how the sensor of FIG. 1 can be used to detect the presence of ferrous metals and stainless steel among non-ferrous or non-metallic products or both;

FIG. 10 is a schematic view showing how several of the sensors of the type shown in FIG. 1 can be arranged in a transverse array so as to not only detect the presence of a ferrous metal in a non-ferrous or non-metallic product or a conductive metal in a non-metallic product but, in addition, its transverse position;

FIG. 11 is a schematic view showing a stationary grid formed of several of the sensors of FIG. 1 arrayed to detect the presence as well as the position in two coordinates of a ferrous metal object in a non-ferrous or non-metallic product.

FIG. 12 is a schematic view showing how the field generator/load cell sensor of FIG. 12 can be used to detect variations in the position of ferrous metal inserts in non-ferrous or non-metallic products whether moving or stationary as well as conductive metal inserts in non-metallic products that are moving;

FIG. 13 is a schematic view showing how the sensor of FIG. 1 can be used to detect the presence of a ferrous metal contaminant even in a ferrous metal container as well as in non-ferrous and non-metallic containers whether moving or standing still or, alternatively, conductive metal objects in a non-metallic containers provided that they are moving; and, FIG. 14 is a schematic diagram illustrating a simplified analog type signal processor for processing the output from the field generator/load cell sensors and arrays thereof shown schematically in other figures of the drawings.

DETAILED DESCRIPTION OF THE DRAWINGS

Referring next to the drawings for a detailed description of the present invention and, initially, to FIG. 1, reference numeral 10 has been selected to broadly identify the sensor subassembly which comprises a field generator and a transducer, each having been similarly identified by reference numerals 12 and 14, respectively. Field generator 12 in the particular form illustrated comprises a magnet of the permanent type generating a field F comprised of lines of force 16 which pass through magnetically transparent carrier 18 and into position where the product 20 being tested will enter and intersect these lines of force. It is to be understood, however, that other magnetic field generating devices can be used in place of a permanent magnet such as, for example, those which produce the field F electronically using, perhaps, even superconductive materials.

In the particular form shown in FIG. 1, the product being tested is confined to a container 22. A sensor support plate 24 is shown located beneath the carrier 18 in position to mount the sensor subassembly 10 in proper position relative to the product 20 and its container 22. In like manner, a mounting plate 26 for the transducer 14 is shown attached to the support plate 24.

Transducer 14 comprises a strain gauge or so-called "load cell" forming an operative connection between its fixed support in the form of mounting plate 26 and the field generator 12 which is free to move relative to the carrier 18 as well as the product 20 and its container 22, if any. As will be explained presently, the carrier 18 may, in some instances, comprise a moving conveyor or, alternatively, a fixed supporting surface upon which the product slides past the sensor or perhaps it is laid upon without moving. This field generator/load cell sensor subassembly 10 comprises the basic building block of the metal detection system of the present invention and its many and varied applications will be described presently in connection with FIGS. 9-13 of the drawings, however, before doing so, a bit more should be said about the basic sensor subassembly 10 and some of its variations.

Starting with FIG. 1, the system illustrated is one ideally suited to the detection of ferrous metal contaminants contained within non-metallic products like, for example, foods packaged in an aluminum tray 22. If we assume that the carrier 18 is magnetically transparent and stationary, then it becomes simply a matter of setting the product to be scanned atop the carrier and see if the field generator 12 reacts to its presence since the aluminum tray is also magnetically transparent and, as long as it is not moving, it will produce no eddy currents and, therefore, not be seen by the detector either. Thus, if no ferrous metal contaminant is present, the field generator will not move nor will the load cell 14 detect any movement in the latter, therefore, the product passes the inspection. If, on the other hand, the tray contains a ferrous metal contaminant, it will attract the field generator 12 raising it up slightly; whereupon, the load cell 14 which is mounted to detect any movement in the latter relative to its fixed support 26, will produce an output signal seen by the detector subassembly that has been broadly designated by reference numeral 30.

Perhaps even more significant is the use of the set-up shown in FIG. 1 where the products to be tested are brought to and placed upon a stationary magnetically transparent carrier to test for the presence of ferrous metal objects that are not contaminants at all, but instead, very necessary parts of the assembly. An example might be an aluminum casting containing a pair of ferrous metal springs of different sizes that were inserted automatically and cannot be seen easily once they are in place. By any other method, this situation presents a very difficult problem to solve; however, using applicant's system, not only can the presence of the spring be detected but, if one is missing, the detector can tell which one. Specifically, the detector would be preprogrammed to look for a total amount of deflection in the load cell caused by the magnetic attraction exerted by both springs as they lift the field generator 12. If we assume that the two springs exert different attractive forces due either to their relative size or their distance from the field generator or both, then it becomes a simple matter to even tell which of the two is missing. Such a system works extremely well in the detection of ferrous metal parts in magnetically transparent metal assemblies that are not moving relative to the sensor.

It is also significant to note that the system as above-described can in most instances be used to locate even stainless steel inserts because, for all practical purposes at least, most stainless steels include enough iron that if the sensor is sensitive enough, the field generator 12 should react to its presence in such a way that the load cell responds to its movement. This is especially true when, as will be seen presently, there are several ways of building the system such that small highly-sensitive load cells can be accommodated even with field generators that are quite heavy because of the high flux densities needed to "see" the stainless steel part or contaminant.

The same system is effective to locate ferrous metal parts in non-metallic products packaged as shown in FIG. 1 in conductive metal containers that are moving by the sensor subassembly 10 on a non-metallic conveyor of some sort that is also moving, however, this becomes a bit more difficult and it entails preprogramming the system to ignore the presence of the container 22. In other words, all metals react in some way when brought into the presence of a magnetic field. Conductive metals like aluminum, copper, brass and others when moving perpendicularly through a magnetic field like field F, have eddy currents induced in them which, in turn, effect the field generator 12 and cause it to respond by either moving toward the conductive metal or away from it. Obviously, once the generator responds to the presence of the conductive metal moving through its field, this movement is sensed by the load coil 14 which, in turn, sends its message to detector 30. The particular effect that the conductor has upon the field F depends upon a number of factors like, for example, its flux density, the speed with which the conductor moves through the field and its size. Whether the conductor attracts the field generator or repels the latter is unimportant since it is a simple matter to set the triggering threshold of the detector circuit to ignore its presence when moving through the field at the speed and in the location it will occupy during normal operation. Then, any deviation from this norm will signify the presence of a foreign object having a ferrous metal component and cause the sensor to react differently than it would react in the presence of the conductor alone which deviation is a simple matter to detect.

Conceivably, the carrier 18 in the form of a moving conveyor could also be made of a magnetically transparent metal and its effect upon the field F "nulled out" so to speak, however, the inherent non-uniformity in the conveyor itself, the presence of metal fasteners and joints that vary in size and location, and the vibratory factors involved which effect the magnitude of the eddy currents, make this a very difficult proposition to handle and one, therefore, that is best avoided.

There are, of course, many variables which influence the size and strength of the field generator needed to accomplish a given metal detection function. They have to do with such things as the size of the product being tested; how far away from the sensor the part to be detected is likely to lie; the nature of the item to be detected, i.e. its shape, size and orientation; whether it is moving or still; its environment in terms of being in a non-metallic product, a non-ferrous metallic one or a ferrous subassembly, etc. While these and other factors influence the requirements of the field generator in terms of its size, weight, location and design, the characteristics of the generator, in turn, have a profound effect on the load cell. In general, the higher the flux density required of the field generator, the heavier and larger it gets. By the same token, the heavier the field generator, the larger the load cell that is required to support it and, the bigger the load cell, the less sensitive it becomes because its electronic resolution suffers to the point where it is unable to detect small load variations. Accordingly, it becomes very significant in those applications where near maximum sensitivity is required to be able to use those load cells having a high resolution but a lesser load-carrying capacity.

One solution to this problem is shown in the modifications of FIGS. 2, 3 and 4, each of which has to do with lightening the load on the load cell 14 by using a ferrous metal element 32 in position to attract and thereby lift the field generator part way up. In the modification 10M of FIG. 2, for instance, a pair of ferrous metal bars 32 would be located in fixed position underneath the carrier on a suitable support (not shown) and within the field F so as to elevate and partially unload the load cell 14. With the static load on the load cell thus decreased, a smaller one can be used which has better electronic resolution and a corresponding increase in its sensitivity. Obviously, the ferrous metal elements 32 must not touch the field generator 12 at any time but lie in spaced relation above the latter even when it is being attracted to a ferrous metal part or contaminant P contained within the product 20 being tested. In the modification 10N shown in FIG. 3, the two ferrous metal bars have been replaced by a ferrous metal screen 32M located above the field generator but underneath the ferrous metal object P as shown. The same requirements with regard to spacing of the screen relative to the field generator exist in the FIG. 3 modification as was true for that of FIG. 2.

On the other hand, the FIG. 4 modification 10P differs from the other two in that the ferrous metal member 32, in this case a plate 32N is spaced on the opposite side of the field generator from that which the product 20 and any ferrous metal part P will occupy. In other words, a gap 34 exists between the field generator and the plate 32N through which the product and any ferrous metal piece P that is present must pass. Once again, the plate 32N is stationary while the field generator is free to move relative to the plate but not so far as to come into contact therewith or, of course, the product.

While the gap 34 is somewhat limiting in terms of the size of the product that can pass between the field generator and plate 32N, nevertheless this modification has certain advantages.

Looking briefly at FIG. 5, the field F shown in this figure is fairly representative of that which would exist around the field generator 12 if arranged as shown in FIG. 1. Adding ferrous metal bars 32 as shown in FIG. 2 or a ferrous metal screen 32M as seen in FIG. 3 will raise the field slightly above that shown in FIG. 5 but not to any great degree. In FIG. 6, on the other hand, where the plate 32N is on the other side of the gap 34 through which the product passes, the field F is raised up considerably higher and it can be shown that its flux density nearly doubles adjacent the plate. Plate 32N still, of course, exerts an attractive force upon the field generator effective to partially unload the load cell as was true of the embodiments of FIGS. 2 and 3 but, in addition, its placement increases the flux density within the gap 34 which is the only area in which it is functional thereby enlarging the overall scanning area within which the system is effective.

A further modification 10Q is shown in FIG. 7. In this embodiment, the basic sensor subassembly 10 of FIG. 1 consisting of the field generator 12, the load cell 14 and the supports therefor (not shown) are all present along with a carrier for the product being examined (also not illustrated) and, in addition, a second field generator 12M mounted above sensor subassembly 10 held in fixed spaced relation to the latter by mounting fixture 36. As was the case in FIG. 1, the field generator 12M has been illustrated as being in the form of a permanent magnet but other generators capable of producing a field F could, of course, be substituted for either of the permanent magnets. The fixture 36 which maintains the fixed spaced relation between the two field generators 12 and 12M could, of course, be made of either a magnetic material or a ferrous one as well as, of course, a non-metallic one.

What makes the system 10Q of FIG. 7 unique is the fact that gap 34 contains two overlapping fields, F and F', the latter being generated by generator 12M. The net result is a much larger scanning area within the gap 34 than can reasonably be produced by a single sensor subassembly 10 of the type shown in FIG. 1 In addition, however, the system 10Q functions somewhat differently. As was the case before, a ferrous metal part P within the field F of sensor subassembly 10 will decrease the load on the load cell 14 and thus output a signal to detector 30 much the same as that of FIG. 1. On the other hand, a ferrous metal part P' that passes above center and within the field of generator 12M will increase the load on the load cell outputting a signal to the detector 30 of the opposite sign. It is, of course, possible that a ferrous metal part could occupy an equilibrium position within the intersection of the two fields F and F' in which the load on the load cell would be neither increased or decreased thus sending no signal to the detector whatsoever indicating the presence of the part P, however, this would be very rare indeed.

The last of the modifications 10R is shown in FIG. 8 and it is designed primarily for use in the detection of small non-ferrous conductive metal parts although it could be used in other applications where an extra high degree of sensitivity is required. A conductive metal part C, especially a small one, will have relatively small eddy currents induced in it when moving perpendicularly through a magnetic field. If the part is small and moving rather slowly, the resulting eddy currents may be too small to detect with a system like that shown in FIG. 1 for example. Conversely, the faster the part moves through the field, the greater the eddy currents induced in it and the easier these are to detect. Accordingly, since there are oftentimes practical limits as to how fast the conductive part C can be moved by a carrier (not shown) through the field, applicant has found the answer to be one of increasing the relative speed by moving the field in countercurrent flow relation to the direction of part movement. This is accomplished as seen in FIG. 8 by mounting the field generator 12N for rotational movement about an axis midway between the poles on a yoke-type supporting fixture 36M preferably made of a non-metallic material. With the part moving to the left as seen in FIG. 8 and the field generator 12N being rotated clockwise, the part will cut the lines of force at a significantly increased rate thus inducing in it much larger and more easily detected eddy currents. Some increase in the eddy currents could be produced by turning the field generator in the same direction in which the part is moving but at a faster speed, however, this is counterproductive since much greater relative movement can be accomplished without having to turn the generator as fast by turning it in the opposite direction.

Directing the attention next to the schematic views of FIGS. 9-13, each shows a slightly different application of the metal detection technology forming the subject matter of the present invention. Starting with FIG. 9, it basically shows a set up like that which has already been described in connection with FIG. 1. The sensor subassembly 10 would be of the type shown in FIG. 1 in most instances since it is being used to detect a ferrous metal part P or a stainless steel one having a detectable ferrous metal component. Conveniently, these sensor subassemblies can include a light-emitting diode which provide visual indications concerning the presence, or sometimes the absence, of a part or the presence of a contaminant. This is not to say, however, that other of the systems already described which have greater sensitivity might not be used if the application demands more than that available from the simple system of FIG. 1. The detector 30 will, in this instance, merely receive a signal from the sensor subassembly indicating the presence of the part P among the product 20 which, as illustrated, is a non-metallic particulate one.

The application of FIG. 10 is somewhat more complicated in that it includes a transversely-extending array 38 of individual sensor subassemblies 10 arranged across the carrier 18 in position whereby each individual subassembly defines a more or less discrete field which preferably overlaps those one either side thereof only to a somewhat limited degree. When arranged in this manner, the system is not only capable of detecting a ferrous metal or stainless part in non-ferrous or non-metallic products along with conductive metal parts in non-metallic ones but, in addition, the location of the part detected in relation to the side margins of the product as it moves perpendicular to the array. By using digital L.E.D.'s, the one directly underneath the part might register an 8 while those alongside only a 4 thus indicating where the part is located.

By way of contrast, the FIG. 11 application is yet a further extension of the one-dimensional array 38 of FIG. 10 wherein the array 40 is two-dimensional and includes a plurality of individual sensor subassemblies 10 arranged in side-by-side relation both transversely and linearly as shown. This setup differs from the one shown in FIG. 10 in yet another way in that the product 20 does not move relative to the array, but instead, stays in a fixed position thereabove as shown. It is only when the product and array are maintained in fixed positions relative to one another that the potential of the system is fully realized in that the location of ferrous metal parts P and P' within the product 20 can be defined by two coordinates instead of just one. A system like that shown in FIG. 11 is, for example, ideally suited for use in that application described previously in which the observer needs to know whether both of the two ferrous metal or stainless springs are present in an aluminum casting. Again we have a situation in which a grid of several digital L.E.D.'s forming parts of the detector 30 will reveal a two-dimensional plot of just where the parts P and P' are located in the product. Again, while several of the L.E.D.'s might be activated, the one displaying the highest digit will be the closest to the part activating the array. This system, of course, is unsuitable for use in detecting the presence of conductive metal parts or pieces because they must move through the field in order to have eddy currents set up in them.

The applications shown in the schematics of FIGS. 11-13 are all shown using a transversely-elongate sensor subassembly 10S which essentially spans the width of the path along which the product being tested moves.

In FIG. 12 a transversely-elongate sensor subassembly 10S is shown in use for detecting variations in the position of the part P from product to product. Going back again to the spring in the casting example already alluded to on a couple of other occasions, the FIG. 12 arrangement would reveal that, while the spring was present, it had somehow fallen out or otherwise moved from the position it should occupy. A suitable L.E.D. display of the part position within the product is easily attained.

The last of the several applications of the sensor subassembly 10S has been illustrated in FIG. 13 and it is that of detecting the presence of ferrous metal contaminants in non-metallic containers, non-ferrous metal ones and even ferrous metal containers. Here, for instance, the ferrous metal part could be a metal sliver in a can of food.

Finally, with reference to FIG. 14, the detector 30 which processes the signal from the load cell 14 will be described briefly in connection therewith. It comprises nothing more than a conventional analog signal processor wherein the strain gauge, or what has been denominated here as a load cell 14 is excited by a signal applied to it by exciter A3. Changes in the output voltage of the load cell are amplified in amplifier A1 and fed to a low pass filter F1 which has as its function that of increasing the signal-to-noise ratio in the conventional manner. A2 is a comparator which receives the filtered and amplified signal and compares it to a preset value which accommodates normal products and their movement while triggering in the presence of abnormal ones. As an example, it would be preset to ignore the movement of the aluminum container 22 in the FIG. 1 application; the non-ferrous metals, if any, in those of FIGS. 9, 10 and 11; the eddy currents set up in the non-ferrous metal products moving in FIG. 12; and the ferrous metal containers moving past the sensor or sitting atop thereof in the FIG. 13 system. Setting triggering thresholds is old in the art and forms no part of the present invention. Once the triggering threshold is exceeded and a signal gets through the comparator A2, it initiates a response of some sort by actuating the contacts of a relay R. If, for example, the relay has normally-open contacts which close upon its being energized, then an appropriate response might be to set off an alarm or actuate a mechanism (not shown) for getting the abnormal product off the production line or some such affirmative action. On the other hand, the contacts of relay might be normally-closed and wired in the circuit that runs the conveyor, whereupon, when it is energized i the presence of a bad product, its contacts could open thus shutting off the flow of product until the bad one is removed.

It should be pointed out that this system like many others used in metal detection are very sensitive to vibration, therefore, some means will likely have to be provided for either reducing the vibration seen by the sensor subassembly by isolating it mechanically or, alternatively, "zeroing it out" so to speak electronically. This can be accomplished in several ways, many of which are commonplace in the art, and all of which are beyond the scope of the present invention.

What is claimed is:

1. An apparatus for differentiating between a first metal and another material in a product to be tested which comprises:

a fixed support;

first means for generating a magnetic field enveloping the product to be tested for the presence of the first metal, said first means being movable relative to said support and to the product, and said first means being responsive to the presence of at least the first metal within the product to move relative thereto when the product is positioned for testing using said first means;

second means for responding to load fluctuations and being connected between said support and said first means, said second means including strain gauge means for sensing relative movement between said second means and said first means caused by at least the presence of the first metal, wherein said strain gauge means is adapted to sense such relative movement when the product is substantially stationary relative to said first means and said strain gauge means generating an output signal proportional to such relative movement, wherein said output signal quantitatively represents a magnitude relating to the metal content of the first metal and any other metallic material present and said output signal is used in evaluating whether such other metallic material is present; and third means, responsive to said output signal, for taking into account the presence of metallic material other than the first metal, wherein the effect of the presence of metallic material other than the first metal is removed.

2. The apparatus as set forth in claim 1 in which: said first means comprises a permanent magnet.

3. The apparatus as set forth in claim 1 in which: the product is non-metallic and the first metal is a ferrous metal.

4. The apparatus as set forth in claim 1 in which: the product is made of a non-ferrous metal and the first metal is a ferrous metal part contained therein.

5. The apparatus as set forth in claim 1 in which: the product is non-metallic and is packaged in a non-ferrous metal container, and the first metal is a ferrous metal part contained within the product.

6. The apparatus as set forth in claim 1 in which: the product is non-metallic and is packaged in a ferrous metal container, and said first metal is a ferrous metal part.

7. The apparatus as set forth in claim 1 in which: the first metal is a non-ferrous conductive metal and the product is non-metallic, and means for moving the product and the non-ferrous conductive metal through the magnetic field wherein eddy currents are generated in the magnetic field to which said second means is responsive.

8. The apparatus as set forth in claim 1 in which:

said first means is subdivided into a plurality of independent field generators arranged in side-by-side relation to define at least a first transversely-extending array thereof, said generators being effective to segment the magnetic field into a plurality of relatively narrower fields, each of which is individually responsive to the presence of the first metal; and means for receiving output signals from said array, said means for receiving including means for detecting the transverse position of the first metal.

9. The apparatus as set forth in claim 8 in which: said first means is further subdivided into a plurality of transversely-extending arrays located on behind the other to form a grid having a plurality of individual magnetic field generators, said generators being effective to segment said field into a number of relatively smaller discrete fields each responsive to the presence of the ferrous metal part, and in which said receiving means is responsive to the outputs of said generators so as to locate the position of the ferrous metal part in two dimensions.

10. An apparatus for differentiating between a first metal and another material in a product to be tested, comprising:

a fixed support;

means for generating a first magnetic field of one polarity enveloping the product to be tested for the presence of the first metal, said means for generating a first magnetic field being movable relative to said support and to the product, and said means for generating a first magnetic field being responsive to the presence of the first metal within the product to move relative thereto when the product is positioned for testing relative to said means for generating a first magnetic field;

means for responding to load fluctuations connected between said fixed support and said means for generating a first magnetic field, said load-responsive means being adapted to sense the relative movement between said means for generating a first magnetic field and said load-responsive means caused by the presence of the first metal, and said load-responsive being adapted to generate an output signal proportional to such relative movement thereby indicating the presence of the first metal;

means for generating a second magnetic field of opposite polarity to the first magnetic field and being positioned in spaced relation above said means for generating a first magnetic field such that the fields generated thereby reinforce one another; and support means interconnecting both field generating means together for coordinated movement effective to maintain the fixed spaced relation therebetween, wherein both of said field generating means cooperate to define a gap therebetween to receive the product, and said first and second magnetic fields lie in stacked relation one above the other so as to bridge said gap.

11. An apparatus for differentiating between a first metal and another material in a product to be tested, comprising:
  a fixed support;
  means for generating a magnetic field enveloping the product to be tested for the presence of the first metal, said field generating means being movable relative to said support and to the product, and said field generating means being responsive to the presence of the first metal within the product to move relative thereto when the product is positioned for testing relative to said field generating means;
  means for responding to load fluctuations connected between said fixed support and said field generating means, said load-responsive means being adapted to sense the relative movement between said field generating means and said load-responsive means caused by the presence of the first metal, and said load-responsive means being adapted to generate an output signal proportional to such relative movement thereby indicating the presence of the first metal;
  ferrous metal means for attracting the field generating means being positioned in fixed spaced relation thereabove, said ferrous metal means being operative to raise said field generating means a predetermined distance thereby lessening the static load on said load-responsive means.

12. The apparatus as set forth in claim 11 in which: said ferrous metal means for attracting said first means is located in fixed position between said first means and the product.

13. The apparatus as set forth in claim 12 in which: the ferrous metal means for attracting said field generating means comprises a ferrous metal screen.

14. The apparatus as set forth in claim 11 in which: the ferrous metal means for attracting the field generating means is located in fixed position above said field generating means with the product therebetween.

15. An apparatus for differentiating between a first metal and other material in a product to be tested, comprising:
  a fixed support;
  first means for generating a magnetic field enveloping the product to be tested for the presence of the first metal, said first means being movable relative to said support and to the product, and said first means being responsive to the presence of the first metal within the product to move relative thereto when the product is positioned for testing using said first means, wherein the first metal is a non-ferrous conductive metal and the product is non-metallic;
  second means for responding to load fluctuations and being connected between said support and said first means to sense the relative movement between said load responsive means and said first means to generate an output signal proportional to such relative movement; and
  means for moving the product and the non-ferrous conductive metal through the magnetic field wherein eddy currents are generated in the magnetic field to which said second means is responsive and wherein said first means is mounted for rotational movement about an axis perpendicular to the direction for product movement and in which means are provided for rotating said first men as in a direction opposite to that in which the product is moving wherein the eddy currents developed in the conductive metal are increased.

16. A method for differentiating between a first metal and another material in a product to be tested, which comprises:
  generating a magnetic field using field generating means in the area where the product is tested;
  permitting relative movement between said field generating means and load responsive means caused by the presence of at least the first metal;
  sensing said relative movement using a strain gauge, wherein said strain gauge is adapted to sense said relative movement when the product is substantially stationary relative to said field generating means;
  outputting a signal proportional to said movement and representing quantitatively at least the first metal; and
  taking into account the presence of metallic material other than the first metal using said signal to remove the effect of the presence of any such metallic material other than the first metal.

17. The method as set forth in claim 16 in which: the first metal is a ferrous metal and the strain gauge is strained as long as the ferrous metal is maintained within a test area.

18. The method as set forth in claim 16 in which: the first metal is a ferrous metal contained within a non-ferrous conductive metal product;
  said field generating means moves in response to both the ferrous metal and the conductive metal as a result of their traversal past said field generating means; and
  said strain gauge has a first strain level corresponding to the traversal of the conductive metal and the ferrous metal past said field generating means and a second strain level corresponding to the traversal of the conductive metal alone past said field generating means.

19. The method as set forth in claim 16 in which: the first metal is a first ferrous metal and the product contains a predetermined amount of second ferrous metal, wherein said field generating means is attracted toward the product to a lesser degree when only the predetermined amount of second ferrous metal is contained within the product and to a greater degree when both the first ferrous metal and the predetermined amount of second ferrous metal are contained within the product; and
  said strain gauge has a first strain level when both the predetermined amount of second ferrous metal within the product and the first ferrous metal are positioned over said field generating means and a second strain level when only the predetermined amount of second ferrous metal in the product is positioned over said field generating means.

20. The method as set forth in claim 16 in which:
  the first metal is a non-ferrous conductive metal contained within a non-metallic product;
  said strain gauge means is responsive to the presence of the conductive metal due to the presence of eddy currents set up within the conductive metal when the product moves relative to said field generating means; and the response or lack thereof of said strain gauge is used as an indication of the presence or absence of the conductive metal.

21. An apparatus for differentiating between a first metal and another material in a product to be tested, comprising:

a support;

first means for generating a magnetic field enveloping the product to be tested for determining whether the first metal is present, said first means being movable relative to said support and to the product, and said first means being responsive to the presence of the first metal to move relative thereto when the product is positioned for testing using said first means;

load responsive second means connected between said support and said first means for sensing relative movement between said first means and said support and generating an output signal proportional to such relative movement to provide an indication of the presence of the first metal; and means associated with said first means for adjusting the position of said first means to lessen the static load on said second means and thereby improve the electronic resolution of said second means for detecting relatively small load variations.

22. A method for differentiating between a first metal and another material in a product to be tested, comprising:

generating a magnetic field using a magnetic field generator;

positioning a product to be tested in a suitable location relative to the magnetic field;

sensing movement of said magnetic field generator using load cell means and generating an output to provide an indication of the presence of the first metal; and unloading said load cell means by adjusting the position of said magnetic field generator to decrease the load on said load cell means and thereby improve the electronic resolution of said load cell means.

* * * * *